US010188512B2

(12) United States Patent
Angheloiu

(10) Patent No.: US 10,188,512 B2
(45) Date of Patent: Jan. 29, 2019

(54) REVERSIBLE CAVITARY TENSION MEMBRANE

(71) Applicant: George O. Angheloiu, Dubois, PA (US)

(72) Inventor: George O. Angheloiu, Dubois, PA (US)

(*) Notice: Subject to any disclaimer, the term of this patent is extended or adjusted under 35 U.S.C. 154(b) by 838 days.

(21) Appl. No.: 14/586,258

(22) Filed: Dec. 30, 2014

(65) Prior Publication Data

US 2015/0184762 A1     Jul. 2, 2015

Related U.S. Application Data

(60) Provisional application No. 61/921,937, filed on Dec. 30, 2013.

(51) Int. Cl.
*A61F 2/24*     (2006.01)
*A61F 2/04*     (2013.01)
(Continued)

(52) U.S. Cl.
CPC ............ *A61F 2/2418* (2013.01); *A61B 5/042* (2013.01); *A61B 5/046* (2013.01); *A61B 5/0464* (2013.01);
(Continued)

(58) Field of Classification Search
CPC .......... A61F 2/2418; A61F 2/04; A61F 2/042; A61F 2/0063; A61F 2/0464; A61F 2/24;
(Continued)

(56) References Cited

U.S. PATENT DOCUMENTS 3,232,787 A    2/1966   Bennett
5,578,069 A * 11/1996   Miner, II ............. A61N 1/0504
                                                         607/122

(Continued)

FOREIGN PATENT DOCUMENTS

SU           1023210 A    6/1983
WO    WO 96/11721 A1    4/1996
WO    WO 97/23729 A1    7/1997

OTHER PUBLICATIONS

Alter, Lloyd, Inflatable Tea House by Kengo Kuma, Online Article, Feb. 17, 2008, http://www.treehugger.com/sustainable-product-design/inflatable-tea-house-by-kengo-kuma.html.

*Primary Examiner* — Walter B Aughenbaugh

(57) ABSTRACT

The present invention's goal is to devise an apparatus (here-forth called 'punch-ball') made of a tension-reversible membrane that will assume a particular three-dimensional predetermined shape when under tension, apparatus that will border a central empty space, central space limited by the interior face of the membrane, and central space that will be in direct communication with the exterior space outside of the external face of the 'punch-ball' through orifices in the membrane (here-forth called 'punches'), punches that will not decrease the ability of the membrane to exhibit a tension force. The punch-ball can be used freestanding or in connection with an object representing a confined space that will be abutting the exterior face of the punch-ball when the punch-ball is under tension. The punches will allow fluid to flow freely or solids to be transferred freely between the interior and exterior of the punch-ball membrane without any limitations to the initial flow through the cavity prior to the punch-ball membrane being deployed in the cavity, the interior face of the membrane being defined as surrounding the empty space inside the punch-ball while the exterior face of the membrane as facing the exterior of the punch-ball. The membrane will be provided with hinge borders (borders that will lack completely or partially the property of being under tension, and at same time have various degrees of elasticity or deformability), borders that will allow the punch ball shape to adapt to the shape of the cavity in which it will be deployed, or for the action to be undertaken. At the end of the action performed the tension in the membrane will (Continued)

cease, the punch-ball will be un-deployed and then removed from the location of action.

10 Claims, 11 Drawing Sheets

(51) Int. Cl.

| | | |
|---|---|---|
| B32B 1/08 | (2006.01) | |
| A61F 2/00 | (2006.01) | |
| A62B 1/20 | (2006.01) | |
| A61B 18/14 | (2006.01) | |
| B32B 27/12 | (2006.01) | |
| C08F 255/00 | (2006.01) | |
| A61B 5/046 | (2006.01) | |
| A61B 5/0464 | (2006.01) | |
| F16L 55/163 | (2006.01) | |
| A61B 5/042 | (2006.01) | |
| A61F 2/06 | (2013.01) | |
| A61B 5/021 | (2006.01) | |
| A61M 37/00 | (2006.01) | |
| A61B 17/00 | (2006.01) | |
| A61B 18/00 | (2006.01) | |
| A61B 18/02 | (2006.01) | |
| A61B 34/20 | (2016.01) | |

(52) U.S. Cl.
CPC ........ *A61B 18/1492* (2013.01); *A61F 2/0063* (2013.01); *A61F 2/04* (2013.01); *A61F 2/24* (2013.01); *A62B 1/20* (2013.01); *B32B 1/08* (2013.01); *B32B 27/12* (2013.01); *C08F 255/00* (2013.01); *F16L 55/163* (2013.01); *A61B 5/021* (2013.01); *A61B 2017/00106* (2013.01); *A61B 2018/0022* (2013.01); *A61B 2018/00351* (2013.01); *A61B 2018/0212* (2013.01); *A61B 2034/2065* (2016.02); *A61B 2505/05* (2013.01); *A61F 2/06* (2013.01); *A61F 2002/043* (2013.01); *A61F 2002/044* (2013.01); *A61F 2002/045* (2013.01); *A61F 2002/046* (2013.01); *A61F 2002/047* (2013.01); *A61F 2002/048* (2013.01); *A61M 37/0015* (2013.01); *Y10T 137/0491* (2015.04); *Y10T 137/0497* (2015.04); *Y10T 428/1352* (2015.01); *Y10T 428/1376* (2015.01); *Y10T 428/1383* (2015.01)

(58) Field of Classification Search
CPC .. A61F 2002/043–2002/048; Y10T 428/1352; Y10T 428/1376; Y10T 428/1383; B32B 1/08
See application file for complete search history.

(56) References Cited

U.S. PATENT DOCUMENTS

| | | |
|---|---|---|
| 5,679,399 A | 10/1997 | Shlenker et al. |
| 6,451,052 B1 | 9/2002 | Burmeister et al. |
| 6,867,533 B1 | 3/2005 | Su et al. |
| 6,969,395 B2 | 11/2005 | Eskuri |
| 6,994,723 B1 | 2/2006 | McMahon |
| 7,354,419 B2 | 4/2008 | Davies, Jr. et al. |
| 7,618,432 B2 | 11/2009 | Pederson et al. |
| 7,722,578 B2 | 5/2010 | Arney et al. |
| 7,777,399 B2 | 8/2010 | Eidenschink et al. |
| 7,914,487 B2 | 3/2011 | Davies, Jr. et al. |
| 7,919,910 B2 | 4/2011 | Eidenschink et al. |
| 7,951,186 B2 | 5/2011 | Eidenschink et al. |
| 8,002,741 B2 | 8/2011 | Hayes et al. |
| 8,002,744 B2 | 8/2011 | Pepper et al. |
| 8,221,351 B2 | 7/2012 | Pepper et al. |
| 8,236,221 B2 | 8/2012 | Pepper et al. |
| 8,313,601 B2 | 11/2012 | Pepper et al. |
| 2009/0259246 A1 | 10/2009 | Eskaros et al. |
| 2010/0145462 A1 | 6/2010 | Ainsworth et al. |
| 2010/0331949 A1 | 12/2010 | Habib |
| 2011/0230952 A1 | 9/2011 | Kassab et al. |

\* cited by examiner

Detail

REVERSIBLE CAVITARY TENSION MEMBRANE

CROSS-REFERENCE TO RELATED APPLICATIONS

This patent application claims the benefit of U.S. Provisional Patent Application No. 61/921,937, filed Dec. 30, 2013, which is incorporated by reference.

BACKGROUND OF THE INVENTION

Various medical and industrial activities necessitate the presence of a object able to put uniform pressure of various magnitudes on the interior of a certain chamber of interest, or to make measurements simultaneously and reliably or move various parts of a chamber of interest or various unattached members, while allowing fluids or solids to transfer freely and unobstructed as compared to the initial state between the interior and exterior of said object or between the attached or unattached members. Such examples include but are not limited to industry and medical applications, such as in interventional cardiology and electrophysiology, where a bodily cavitary chambers of various volumes and shapes need to be investigated or intervened upon with the help of an expanding object that occupies the entire cavity in order to uniformly touch the walls of the cavity, while fluids or solids still are able to transfer through the cavity with approximately no limitation to the initial flow existent in the cavity prior to the object being deployed or prior to the object being present in the cavity. Similarly one can imagine applications in industry, such as in the repair of pipelines, where one needs to obstruct puncture damages in the pipes while still allowing an unobstructed flow through the pipe similar with the flow prior to the pipe being repaired, or in construction where one needs to deploy quickly and simultaneously a number of attached or unattached members, while being able to work on these members while being surrounded by them. Other applications of such a device can be imagined, and they will be exemplified below.

There are no such devices in use so far. While some medical applications such as stents, can apply pressure on the walls of the chamber they have been inserted into (such as arteries as veins), majority of them prevent completely the flow through the chamber of interest (U.S. Pat. No. 7,354,419 to Davies et al.; U.S. Pat. No. 7,777,399 to Eldenschink et al.) while some (U.S. Pat. No. 7,618,432 to Pedersen et al.) allow minimal partial flow through a central channel. The latter invention cites aortic valve angioplasty balloon provided with a channel for perfusion of the rest of the body during the balloon valvular procedure. However this provides only a partial transit of the cardiac flow. If a complete flow transit would have been allowed through the balloon, no space would have been left for the actual balloon device to be inserted and inflated in this particular invention.

BRIEF SUMMARY OF THE INVENTION

We propose the object of the present apparatus (hereafter called punch-ball) to have the following properties in order to be able to undertake the above actions:

the walls of the punch-ball will be made of a membrane supposed to be a thin membrane (thickness less than approximately ⅕ of the average diameter of the empty space that the membrane surrounds)

punch-ball will border a central empty space, central space limited by the interior face of the membrane, and central space that will be in direct communication with the exterior space outside of the external face of the 'punch-ball' through orifices in the membrane (here-forth called 'punches'), such as in FIGS. 1a and 1b.

the material membrane that the punch ball is made of has to have high tensile strength (this will allow pressure with little deformation of the material, allowing the empty space that the punch ball surrounds not to occlude), medium elasticity, and allow processing into thin sheets. Polyethyleneterphtalate and carbon nanotubes may be two such materials.

the above membrane will actively expand and shrink as a result of 4 mechanisms that will finally exert a tension force in the plane of the membrane, mechanisms listed below, but not limited to these mechanisms the punch-ball when deployed will uniformly circumferentially touch the walls of the cavity in which they will be introduced at least in one plane of the three-dimensional space, when deployed in a cavity.

the punch-ball walls will deploy pressure of graded, uniform and temporally stable intensity on the cavity walls in which will be deployed, when deployed in a cavity.

the punch-ball will allow the transfer of the fluids or solids through its empty space, by being provided with punches approximately similar with the inlets and the outlets of the cavity in which they will be deployed, as in FIGS. 1a and 1b.

the punch ball membrane will eventually be able to adapt to the shape of the cavity when deployed in cavities of irregular shape, by being provided with hinge borders where tension force is not present or diminished and also by being provided with tension force directions adapted to the shape that needs to be achieved, such as in FIG. 2.

DETAILED DESCRIPTION OF THE INVENTION

Listed below are 4 examples of the mechanisms that would allow a tension force to be applied in the plane of the punch-ball membrane. While using any of these mechanisms the pressures in the cavity before and after the punch-ball will stay approximately unchanged with those prior to the punch-ball being deployed and the flow through the cavity of interest with the punch-ball deployed will be approximately similar with the flow through the cavity with the punch-ball being in the cavity but un-deployed or outside the cavity.

In a first example, the membrane can be a double layer membrane or membrane made of one or more layers made of various plastic materials (polyethyleneterphtalate, and carbon nanotubes might be two such materials) or any other type of materials that can be subjected to processing into thin sheets and with the material properties listed above.

Figure 3:
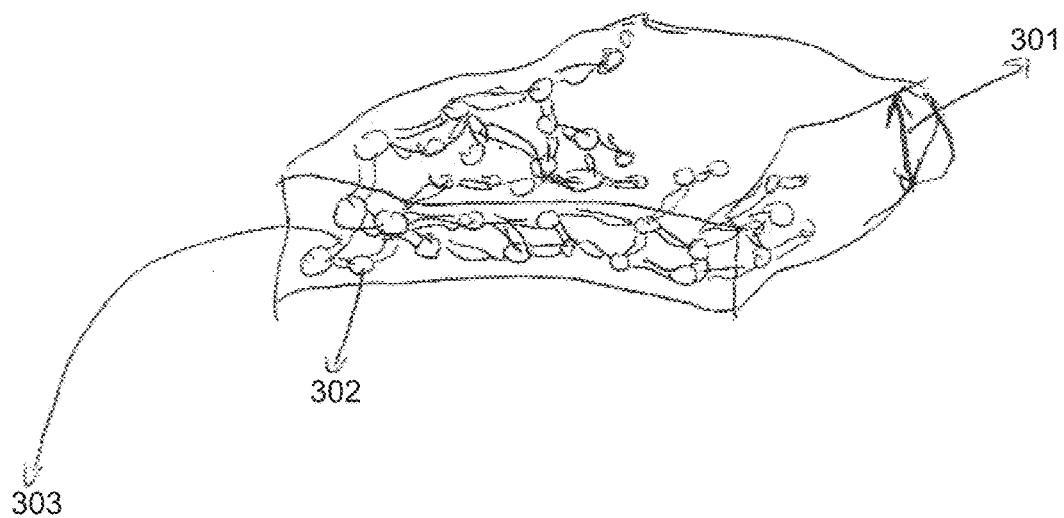
FIG. 3. Thickness of the punch-ball membrane, consisting of one layer displaying internal vacuolated cavities communicating by internal channels. A fluid injected under pressure in the vacuoles will initiate a tension force in the plane of the membrane.
Figure 4A:
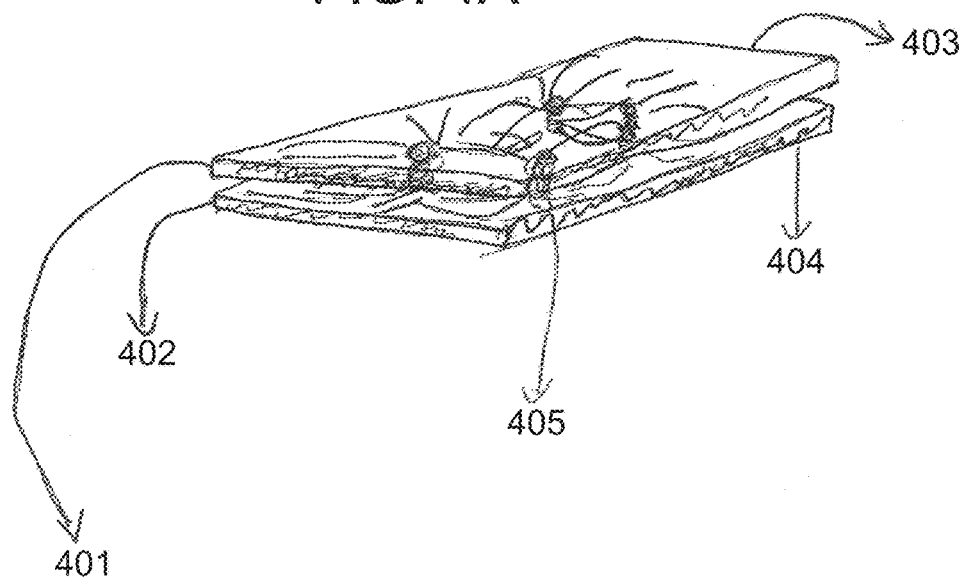
FIG. 4. Punch-ball membrane made of two layers united by spots where the two layers are melted, fused, glued or united together by any other means (4a), or where the two layers are brought in close proximity by fibers that interwove between the two layers (4b).
Figure 4B:
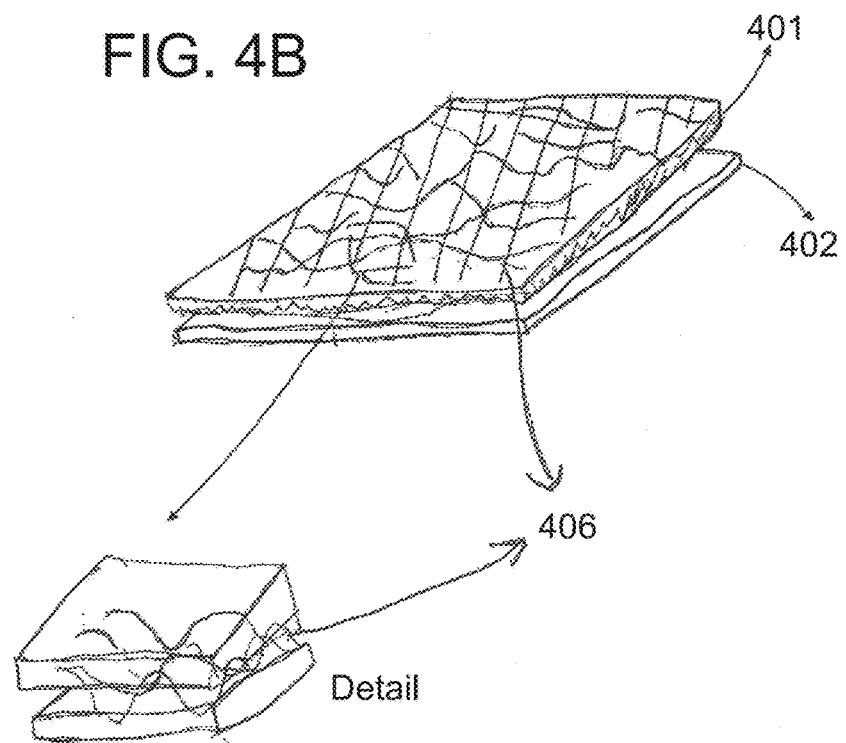

The membrane can be made of one polymeric plastic material sheet with a multitude of vacuolated spaces inside the thickness of the membrane (FIG. 3), all in communication with each other, vacuolated spaces that have the purpose of being filled with a fluid under pressure and in this way exerting a tension pressure in the plane of the membrane. If the membrane is made of two separate layers, the two layers will attach to each other in defined areas by fusion, gluing or melting or any other process (FIG. 4a), or come in contact by fibers that interwove between the two layers (FIG. 4b). In this way the two layers of the membrane will be in close approximation to each other. The distance between the layers will be approximately less than 1/10 of the average diameter of the empty space that the membrane surrounds. The external layer of the punch-ball has a face towards the exterior of the punch-ball membrane (exterior face of the punch-ball) and one towards the internal layer. The internal layer of the punch-ball membrane has a face towards the external layer of the punch-ball membrane and one towards the empty space of the punch-ball (internal face of the punch-ball). As shown in FIGS. 4a and 4b, the membrane includes: external layer of punch-ball 401; internal layer of punch-ball 402; external face of punch-ball membrane 403; Internal face of punch-ball membrane—towards the punch-ball's empty space 404; spots where the membrane was fused, glued, melted together or kept in touch by any other method 405; and threads passing from one layer to the opposite to keep them in close proximity 406.

At the edges of the membrane fabricated in the two ways (two layers untied at various spots or layers united by interwoven fibers) the two layers will be fused, glued or melt by any other process, or in continuation of each-other creating in this way a closed thin chamber. This closed chamber is in fluid continuation with one or a multitude of tubes through which a fluid such as liquid or gas can be introduced under pressure into the chamber created between the two said layers or in the numerous cavities inside the membrane. The membrane will expand by introducing fluid under pressure into the membrane, fluid which could be either a gas or a liquid.

A second way to activate a tension force in a punch-ball system would be to embed inside a thin layer or between two glued/fused layers made of plastic material or any other material that can be subjected to processing into thin sheets, electro-magnetic coils of various thicknesses (such as centimeters, millimeters, microns or nanometers), sizes that correlate with the thickness of the plastic layer. The application of a current into the coils in such a way to create magnetic fields of similar or respectively opposite directions will result into a reciprocal force of repulsion or attraction of the electromagnets, resulting into an immediate tension and stretching or shrinking of the membrane and subsequent active expansion or shrinking of the membrane respectively.

A third possible process to cause membrane self-expansion would be to employ thin sheets of shape-changing metals or plastics that could be incorporated into one layer membrane or between two layers that are fused or glued and are supposed to expand, or by incorporating into the particular membranes a multitude of threads that self-expand spontaneously and then retract upon manual or automatic retraction.

In a fourth example, incorporate inside a thin sheet or between at least two sheets of plastic or polymeric materials electro-active polymers that, by changing shape or dimensions in various directions upon application of a voltage, can change the shape and tension of the membrane. Such an example can be found with U.S. Pat. No. 6,867,533 to Su et al.

Figure 1A:
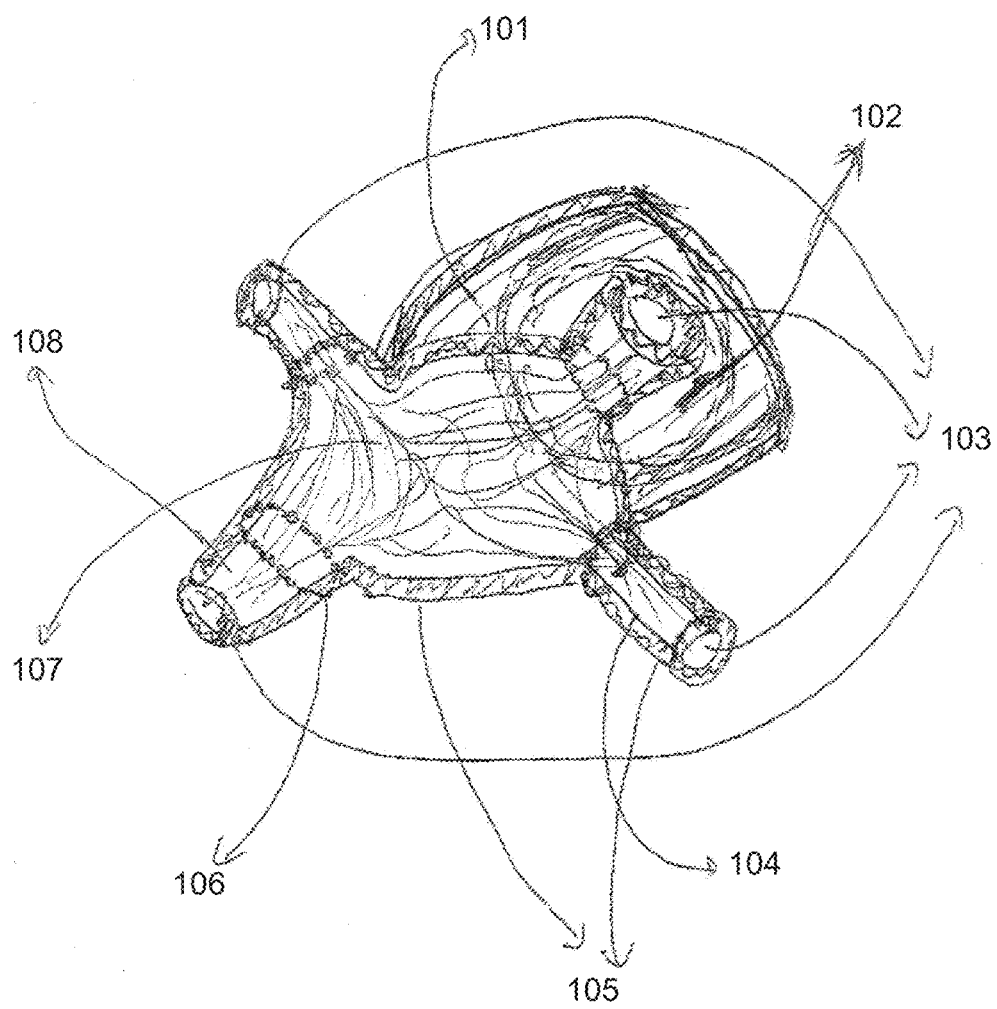
FIG. 1a. Left atrial punch-ball used for uniformly covering the left atrial and distal pulmonary veins internal aspect. Punch-ball is eventually provided with electrodes for procedures of electrophysiology.
Figure 1B:
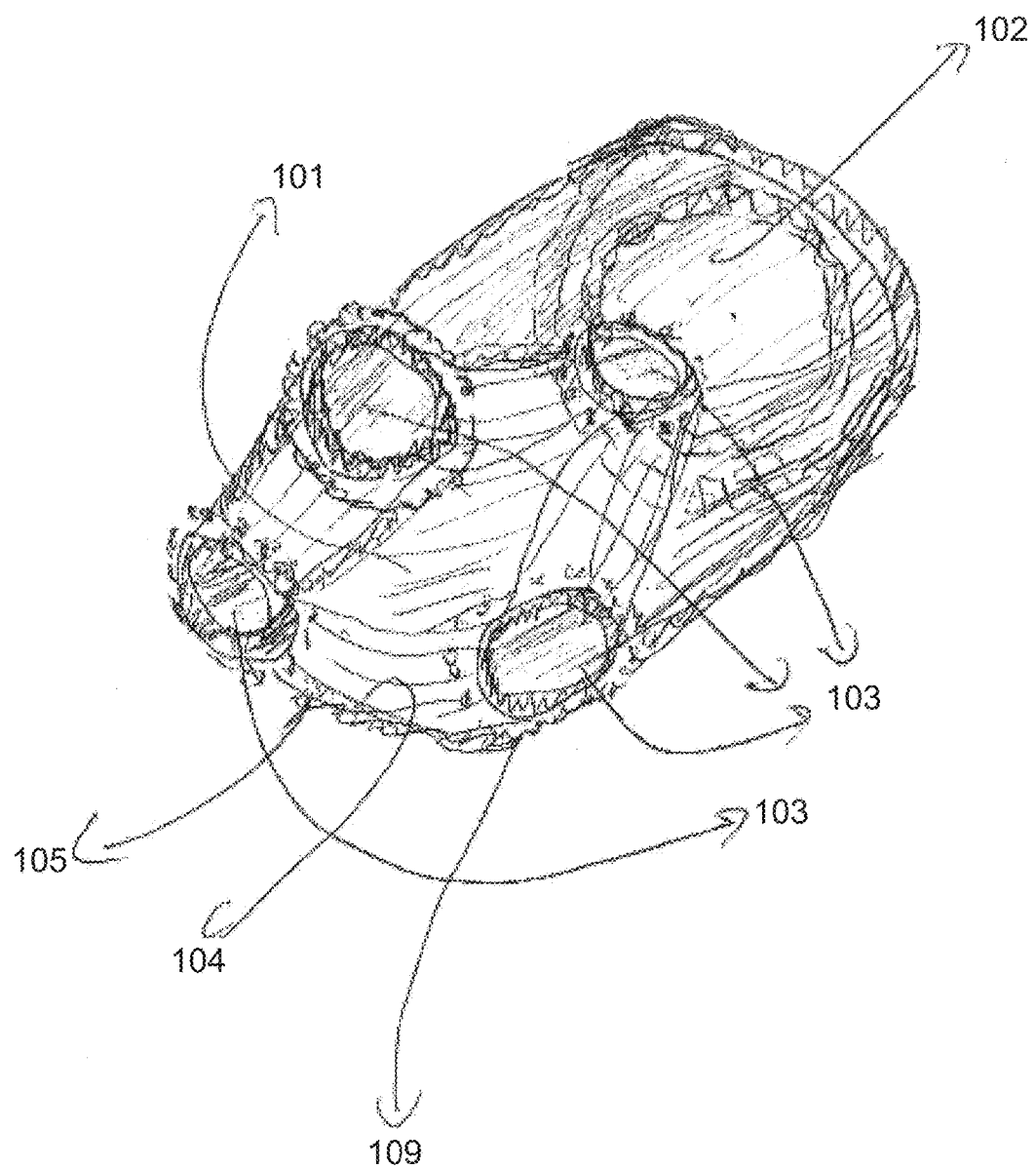
FIG. 1b. In this figure, the left-atrial punch-ball covers only the internal face of the left atrium without entering the pulmonary veins. Electrodes are attached for electrophysiology procedures, and they are located outside and distal to the pulmonary veins.

By exerting a tension force in the membrane's plane through one the four mechanisms described above, the membrane will be able to expand from a 'shrunken' state to an 'expanded' state and assume various shapes in this way when an extension force is applied along the plane of the membrane, such as various geometrical forms, including sphere, ellipsoid, cube, parallelepiped, or any custom-designed surface that will cover by inside a cavitary space of certain predetermined shape as in FIGS. 1a and 1b. By reversing the extension force, the object will actively come back to the initial 'shrunken' state.

Since the membrane is made of one layer or the membrane's edges are sealed when the membrane is made of two layers (this contributing to the creation of a sealed space in-between the two layers of the membrane) then one can imagine that the surface of these geometrical shapes can include open areas or punches such as in FIGS. 1a, 1b, 5, 6, 8, and 9. In this way, depending on the use of the particular membrane, one can envision that the shaped membrane will allow the transfer of objects of solid or fluid nature through the punches, and, in this way, through the virtual plane that the membrane represents.

One can envision using this expanding tension membrane or punch-ball, as mentioned above, in connection with a confined space (category A) or freestanding (category B).

Category A. When used in connection with a confined cavitary space, the punch-ball system will cover partially or completely the internal surface of the particular objects encircling the confined cavitary space with the purpose of putting pressure on the objects that encircle that particular cavitary space or to obliterate orifices inadvertently created in the objects that encircle the particular confined cavitary space. The advantage of this technique is that since the membrane is very thin (less than ⅕ of the diameter of the encircled space) one will cover the internal surface of the targeted confined cavitary space without limiting or obstructing the space confined, and at the same time allowing fluids to freely flow from outside to the inside (and also in the opposite direction) of the confined cavitary space or solid objects to freely transfer from outside to the inside (and also in the opposite direction) of the confined cavitary space. At the same time since the punch-ball membrane can be made of various materials of high strength and endurance, once can imagine as well that the punch-ball membrane can endure and create high pressures such as in industrial applications, or pressures of low magnitude as well, such as in medical applications.

Two general examples can be offered to exemplify the purpose A (of putting pressure on the object that encircles a confined space): one would be the use of punch-ball inside anatomical cavitary organs (version 1), and the second in any mechanical domain where one would like to create a support for an outside structure or create a seal for an outside structure that inadvertently suffered unwanted punctures or damages (version 2).

To exemplify version 1, we will take as target anatomical organs the heart chambers (example "a") or the body vessels, arteries or veins or other organs (example "b").

For example "a": There are at least three instances where an operator would like to have the opportunity to use a thin tension membrane that expands and covers uniformly the interior of a heart chamber and allowing the blood still to flow through it, such as a punch-ball. The first is the occasion of an electrophysiological arrhythmia ablation. The current methodology involves the guidance of a catheter from the venous side into the right or left heart chambers, followed by the application of electrical stimuli in various parts of the heart, recording of the resultant electrical activity contributing to the formulation of an electrophysiological diagnosis, and then application of selective areas of high or low temperature foci or radio-frequency stimuli or cryoablation stimuli to burn ("ablate") the foci or the regions that generate the arrhythmia, while the procedure is performed and monitored under X-ray fluoroscopy. Such test most frequently performed are ablation of arrhythmias such as: supraventricular tachycardia, atrio-ventricular reentrant tachycardia, atrial tachycardia, atrial flutter, atrial fibrillation, ventricular tachycardia, etc, with the latter two being the lengthier and laborious of all. Due to the inability to control the pressure provided by the catheter on the heart tissue or the perfect placement of the catheter, one may risk to create perforation of the heart or esophagus tissue or to provide a lower burning pressure and power, rendering the procedure inefficient. By using a punch-ball one would cover the heart chamber uniformly, and due to the fact that the membrane allows open areas (punches) to be left in its surface, still allow the blood to flow through that particular cardiac cavity while the procedure takes place, giving enough time to the operator to deploy the punch-ball, send the diagnostic stimuli, reach a diagnosis and then perform an ablation by deploying the burning stimuli (which in general are radiofrequency or cryoablation stimuli). The flow through the cavity with the punch-ball deployed will be essentially similar with the flow through the cavity with the punch-ball being in the cavity but un-deployed or outside the cavity. The punch-ball in this case will be composed by a stabilizing portion that covers the free walls of the chamber and the septum separating the right and left chambers (either inter-atrial or inter-ventricular septa), and a portion where the punch-ball membrane would have punches either to the corresponding affluent veins (such as the cava veins for the right atrium or pulmonary veins for the left atrium, or mitral and tricuspid valves for the left and right ventricles respectively) and the effluent outlets (such as the mitral and tricuspid valves for the left and right atria respectively, and the right and left ventricular outflow tracts for the two ventricles). An example of such a punch-ball use can be seen in FIGS. 1a and 1b, where a reversible extension membrane punch-ball is employed in the left atrium for a possible atrial fibrillation ablation. FIGS. 1a and 1b include the following: 101 Punch-ball body occupying the left atrium cavity and covering the punch-ball empty space that allows the blood to flow from the pulmonary veins to the left ventricle; 102 Punch outlet allowing the blood to drain from the punch-ball empty space into the left ventricle through the mitral valve; 103 Punch inlets allowing the blood to enter the empty space of a punch-ball from the pulmonary veins; 104 Internal face of punch-ball; 105 External face of punch-ball; 106 Ablation electrodes situated at the level of pulmonary vein ostium; 107 Posterior wall of punch-ball sits against the posterior wall of the left atrium; 108 Extensions of punch-ball membrane and punch ball empty space protruding into the pulmonary veins; and 109 Ablation electrodes situated around and between the punch-ball inlets and abutting the left atrium posterior wall anterior to the pulmonary vein ostia.

Figure 1C:
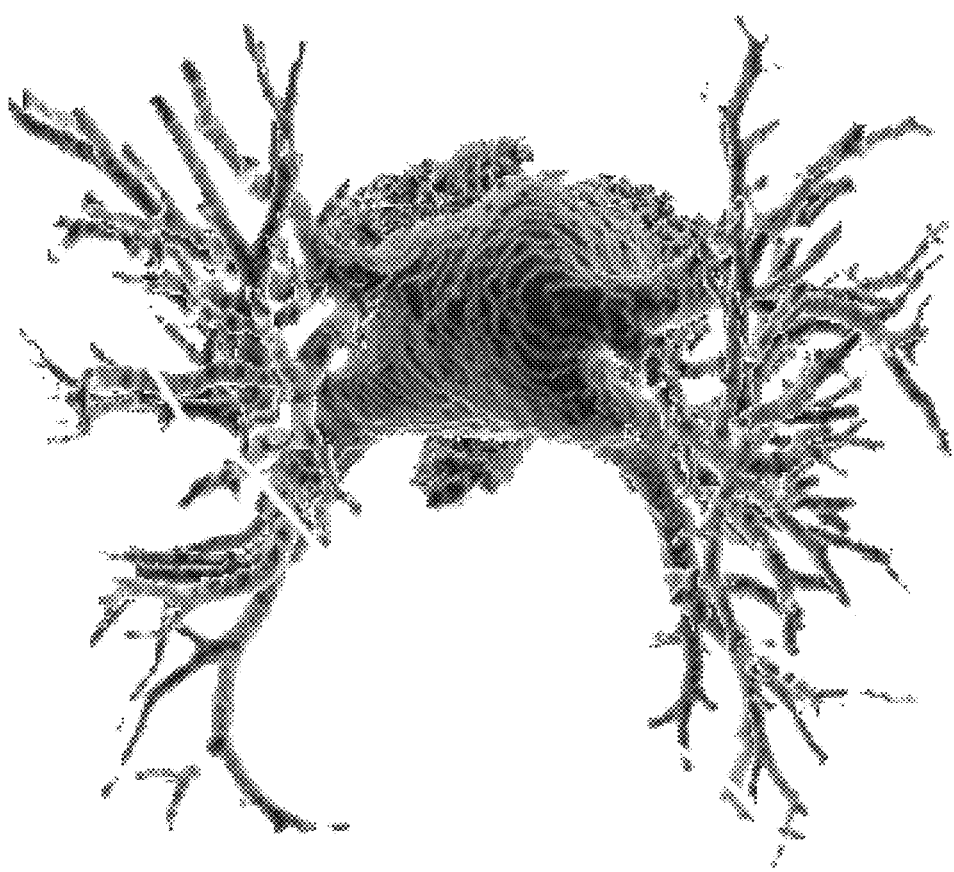
FIG. 1c. Rendering of left atrial posterior aspect and pulmonary veins obtained by means of computerized tomography.

FIG. 1c shows a computerized tomography angiogram of the left atrium, with four pulmonary vein trunks coming out of the posterior wall of the left atrium. In atrial fibrillation the objective is to burn a rim of tissue around the pulmonary veins, in this way preventing the atrial fibrillation stimuli from propagating. For this reason, a reversible cavitary extension membrane will be deployed in the body of the left atrium. Part of the punch-ball can protrude eventuality in the pulmonary veins, as in FIG. 1a, or only come close to the pulmonary vein ostia such as in FIG. 1b. There will be punch orifices in the posterior wall of the punch-ball allowing blood to drain from the pulmonary veins into the punch-ball cavity and from there into the left ventricle through an outlet punch orifice in the anterior wall of the punch-ball. The punch orifices can be arranged and have dimensions of such nature that would allow the use of one generic shape for any type of pulmonary vein disposition. In the later case there will be a unique inlet punch that would allow the drain of the entire pulmonary blood flow into the empty cavity, with a single ablation rim situated slightly anterior to all pulmonary vein ostia.

Figure 2:
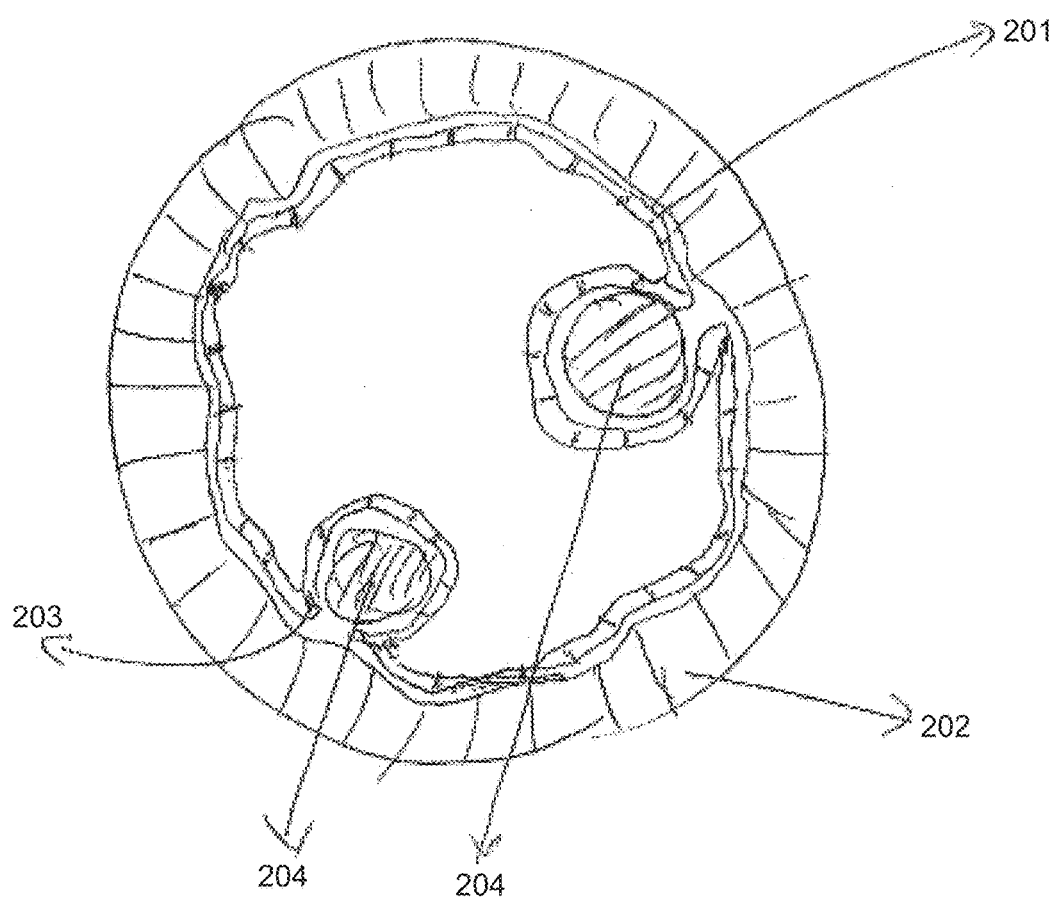
FIG. 2. Punch-ball as seen deployed in a irregular cavity such as the left ventricle. Hinge borders help the membrane to adjust to the irregular cavity walls.

FIG. 2 shows a punch-ball membrane 201 as seen deployed in a irregular cavity such as the left ventricle myocardium 202. Hinge borders 203 help the membrane to adjust to the irregular cavity walls and abut papillary muscles 204.

EXAMPLE 1

To exemplify the method by which the punch-ball will be used in this instance, the punch-ball in the deflated position will be disposed around a wire that will be introduced through a sheath and a catheter into the chamber of interest. Then under X-ray fluoroscopy the operator will position the wire in such a way that when deployed the punch-ball will adopt a position adequate for the electrophysiologic diagnostic and/or ablation procedure. Sometimes the operator may use a "mask" of the chamber of interest generated by a pre-performed test such as cardiac computerized tomography or magnetic resonance of the heart to guide the catheters and wire. The operator will perform the diagnostic procedure and ablation while flow will be able to take place through the cavity of interest. The advantage of using a punch-ball is obviously that the operator can make a multitude of simultaneous diagnostic trials, and afterward perform multiple foci ablation simultaneously, significantly shortening the time of the procedure. Another advantage is the fact that the punch-membrane will offer a more complete coverage of the cavitary wall, not missing any arrhythmia foci in this way. A third advantage is that one can measure and modulate the pressure put by the punch-ball membrane on the walls, in this way assuring efficacy and also safety of the procedure. A fourth advantage is that by offering multiple points of contact, diagnostic procedures will be automatically more successful, since the diagnostic part of the procedure requires most of the time measurements between multiple points along the cavity walls. After the diagnostic and/or ablation procedure, the extension force in the punch-ball will be discontinued, the membrane will come to a resting non-deployed state and then will be removed from the body.

For example "b": The punch-ball's use in human or animal vessels (arteries, veins) as mentioned at point "b" of version 1 can be exemplified by use of this device in the case of aortic dissection, or any tubular organs of the body.

Figure 5:
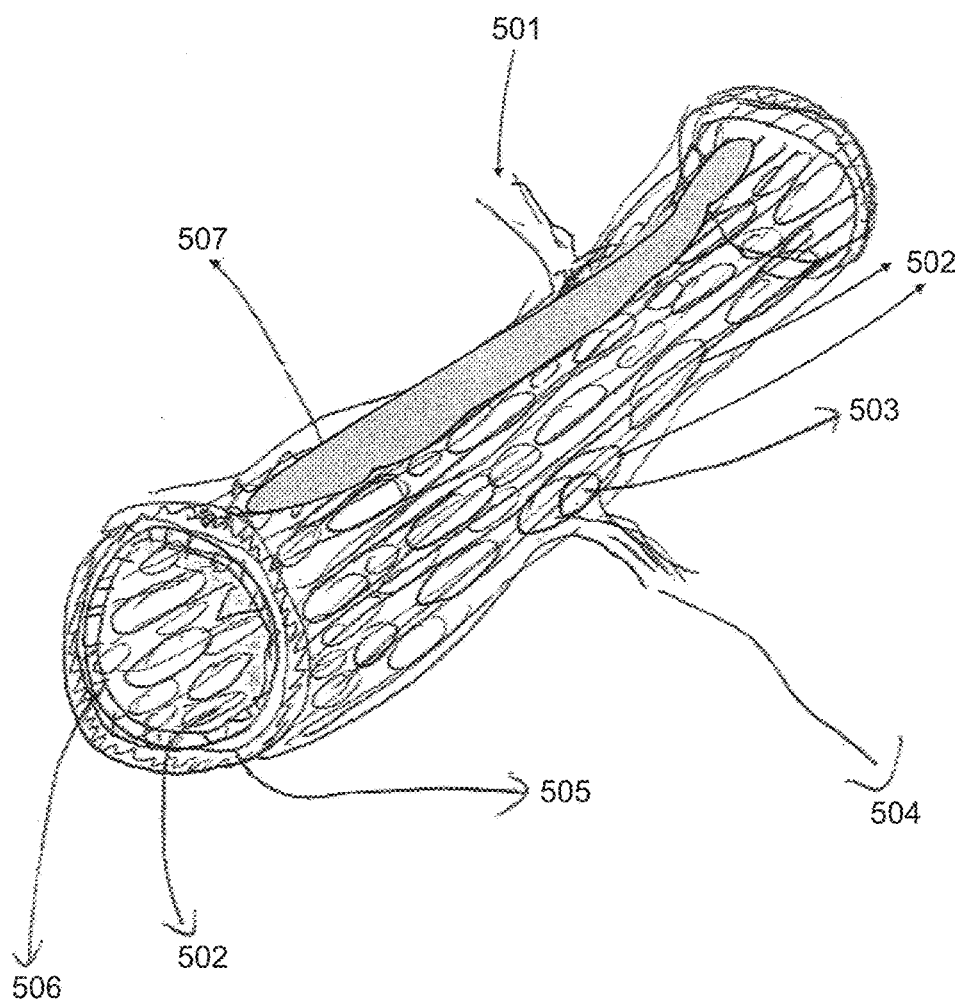
FIG. 5. Aortic dissection treated by deploying a punch-ball that reduces the false lumen, allows blood to pass into the affluent branch arteries and at the same times allows blood to freely flow in the aorta.

The aortic dissection is a condition prevalent in patients with arterial hypertension, atherosclerosis or predisposing genetic conditions, where the inner layer of the aorta (the main artery transporting blood from the heart to the rest of the body) is punctured around atherosclerotic sites. The blood enters these puncture wounds and separates the inner layer (intima) from the medium layer (media) of the aorta creating a second space with non-circulating blood ("false lumen," where lumen means the interior of a hollow body) in the aorta, which in most cases becomes larger than the real lumen. This condition has severe consequences, including severance of the blood flow to critical organs such as the brain, kidney, spine, liver, spleen, gut, or heart muscle, etc., or accumulation of fluid in cavities around the heart and lung creating compression of these organs, followed by shock and death. Currently the treatment of this condition is urgent surgical intervention that involves the replacement of the aortic segment involved with artificial conduits sutured head-to-head to the remaining healthy aortic tissue, or placement in some cases of special large stented artificial grafts. This procedure is available only in tertiary referral centers around the world, and in many cases the transfer time makes the intervention tardy and in the end futile. One can imagine the use of a punch-ball in the shape of a long tubular object with the external diameter similar in size with the lumen of the aorta that can be in the resting position disposed around a wire, which can be introduced in the aorta through a sheath and a catheter by ways of a peripheral artery (FIG. 5). The wire is introduced under fluoroscopy guidance into the real lumen of the aorta, eventually with the help of a "mask" of the aorta generated by a pre-performed test such as cardiac computerized tomography or magnetic resonance of the heart. Then when decided that punch-ball is in appropriate position, the punch-ball will be deployed, putting pressure on the aortic walls, and pressing the blood out of the false lumen. FIG. 5 includes: aortic branch situated in an affected area of a dissected aorta (by reducing the false lumen the branch stays open; a punch orifice allows the blood to flow through the branch) 501; punch orifices 502; branch ostium opening in the aortic lumen through a punch orifice 503; branch artery 504; aortic wall 505; punch membrane 506; and false lumen in an aortic dissection is reduced after the punch-ball expansion 507. Although in FIG. 5 false lumen 507 appears to be on top of artery, it is shown in this manner only for purposes of illustration. In practice, false lumen 507 would be positioned between the arterial wall 505 (i.e., below it in the figure) and the tension membrane 506 (i.e., on top of it in the figure).

In this particular application, the number and sizes of punches on various lateral locations of the punch-ball will vary depending on the size and number of branches in the vessel operated on. The higher the number of branches and the larger the size of these branches, the larger and more numerous will be the lateral punches applied in the punch-ball in order to allow a completely unobstructed flow to or from the branches. The smaller the branches will be in the particular segment covered, the smaller the distance between the punches will be. For example if the punch-ball will be used in the area of intercostal arteries (that have diameter of 1.4 mm at the ostium, van Son J A, "Intercostal artery: histomorphometric study . . . ," Ann Thorac Surg. 1993; 56:1078-81.), the distance between punches will be preferably less than 1 mm, so any artery will have enough blood supply from the aorta. This will allow the blood from the real lumen of the aorta (in the particular application of aorta) to flow into various branches of the aorta, continuing in the is way to perfuse various organs such as brain, kidney, spine, liver, spleen, gut, heart muscle, etc. (FIG. 5).

As one can notice in FIGS. 5 and 1 the vessel punch-ball will be provided at the proximal and distal end with punches that would allow the blood to flow from the heart inside the lumen of the large punch-ball tubular structure and then outside from the distal end punch or the lateral punches to the organs irrigated by the aorta. By deflating the false lumen of the aorta, all deleterious consequences of the dissection created either by blood low severance to critical organs or by blood leakage into cavities surrounding the heart (pericardial cavity) or lung (pleural cavity) will cease. In this way the patient will have enough time to reach a tertiary surgical center and have the final procedure performed.

Alternatively one can imagine a way to keep the punch-ball for a certain period of time in the aorta and allow the intima to re-adhere to the media without surgery. This would allow patients not fit for a major aortic surgery (due to other comorbid conditions) to survive this type of otherwise fatal events. Subsequently with good anti-hypertensive and beta-blocker therapy the patient may avoid or temporize a major surgery.

Another possible use of the punch-ball is to deploy patches to close various congenital or acquired orifices in the wall of various organ cavitary structures. The punch-ball exerts equal pressure on virtually all points of contact without obstructing the flow of fluids in that particular cavity, hence the delivery of a patch to a cavitary wall puncture will be uniform, and followed by a complete and uniform closure. The patch will be situated on and partially adherent to the external face of the punch-ball. The face of the patch opposite to the punch-ball will be eventually provided with a special glue or eventually miniature hooks that will promote complete adherence to the cavity's wall tissue. Upon expansion of the punch-ball the patch will adhere by mediation of the glue or eventually hooks onto the cavity wall. The adherence process will be uniform due to the uniform pressure of the punch-ball. Upon shrinking of the punch-ball the patch will stay adherent onto the cavity wall. Orifices that can be closed in this way are acquired (such as the entry orifice of the false lumen in an aortic dissection or any other of arterial or venous dissection, or acquired shunts) or congenital such of patent foramen ovale, atrial septal defect, ventricular septal defect, patent ductus arteriosus, and the entry orifice of any type of cardiac or vascular shunt.

Another setting where the punch-ball may be useful is the traumatic rupture of the aorta (aortic transsection) where the aorta is torn and completely or partially ruptured after traumatic events involving the chest. These events are many times rapidly fatal, and an early intervention that would stabilize the blood flow to the aorta in a center where cardiac surgery is not available might be life-saving. The punch-ball would be introduced in the aorta similarly with as in the case of aortic dissection and then deployed to keep the aortic conduit open to blood flow and the aortic wall in structural continuity.

Similarly with the aortic dissection, one can image using a punch-ball device in other types of arterial dissections, such as coronary, carotid and other peripheral arteries, when metal stenting is not the best option, such as in cases where the vessel dissects throughout the length of the vessel. Similarly, cases of venous dissection (spontaneous, following stenting or any other type of interventions) or traumatic venous rupture can be treated similarly with the use of a punch-ball device.

After the intervention has ended with an eventual beneficial result, the extension force will be discontinued, the punch-ball membrane will come to a resting non-deployed state and then will be removed from the body.

EXAMPLE 2

Since punch-ball can make complete contact with a tubular structure without occluding the particular structure, one can imagine the possibility of delivering drugs to that particular structure through a punch-ball device with the punch-ball being implanted in that particular structure possibly for a relatively longer period of time. Any tubular structure can benefit from this type of treatment, including gastro-intestinal, genito-urinary, cardiac, vascular or pulmonary structures, but not limited to these, where fluid (air, blood, urine, etc.) or solid materials (food, feces, etc.) have to travel continuously of intermittently through that particular tubular structure. Conditions such as cancers, bleeding, infections difficult to treat, or atherosclerotic lesions could be possible targets. The drugs or any other type of treatments could be delivered to the abutting tissue by various modalities. The punch-ball membrane will be provided with a network of channels inside the membrane such as in FIG. 3, in communication with an external tubular structure that will direct medications to the punch-ball membrane internal network. The punch-ball membrane will have a membrane thickness 301, small cavities inside the punch-ball membrane 302, and channels inside the punch-ball allowing communication between cavities 303.

From this internal network the medication will travel to the abutting tissue through methods including but not limited to small needles (the size of millimeters, micrometers, or nanometers depending of the cavitary organ size of target) originating from the exterior surface of the punch-ball membrane, needles that will insert with the sharp end into the abutting tissue, and needles that will have an internal channel that will conduct the medication from the membrane internal network to the abutting tissue. Alternatively, instead of needles, or by using small external porous orifices from where the medication will freely flow to the abutting tissue. Using the latter option, since the membrane exerts a certain pressure on the cavitary organ's walls, the fluid sipping in-between the membrane and the cavity walls will be under pressure as well, which will favor the distribution of medication into the tissue. At the same time, since the fluid transferred from the external tubular structure into the internal network needs to be under pressure, this fluid will serve as the extension force vehicle that will lead to extension of the punch-ball membrane while at the same time serving the purpose of delivering a medication.

In the instance of medication delivery, once the medication delivery ceased, the extension force will be discontinued, the membrane will come to a resting non-deployed state and then it will be removed from the body.

EXAMPLE 3

One also can imagine the use the punch-ball in the same type of cavitary structures to simply put pressure for a long time on the walls of the organs, with the purpose for example of stopping a bleeding from a bleeding vessel inside the organ's walls, while fluids and solids still can transfer though the cavity. If one would use instead a device that occupies the entire volume of the bodily cavity, this device would need to be used only for a short time due to the necessity to allow the transit of solids or fluids to reoccur, while the punch-ball can lodge in the cavity for a long time without causing a transit blockage. After the bleeding has stopped the extension force will be discontinued, the punch-ball membrane will come to a resting non-deployed state and then will be removed from the body.

EXAMPLE 4

Another reason to use a punch-ball inside any of the cavitary organs described above is to make simultaneous multiple measurements that require close contact, such as spectroscopy, optical and ultrasound measurements (Angheloiu et al., "Detection of coronary atherosclerotic plaques . . . ," Atherosclerosis. 2011; 215:96-102; Angheloiu et al., "Intrinsic versus laser-induced fluorescence spectroscopy . . . ," Appl. Spectrosc. 2012; 66:1403-10; Georgakoudi et al., "Characterization of dysplastic tissue morphology . . . ," Gastrointest Endosc Clin N Am. 2003; 13:297-308). These type of measurements are generally performed in tubular cavitary organs (such as arteries) by introducing along the longitudinal axis of the organ a wire provided at the tip with a sensor, this being subsequently followed by manually or automatically retracting the wire with a sensor at the tip, wire rotating in order to acquire circumferential images or spectra of the organ's wall. However, this method may lead to good data acquisition only in organs whose walls do not retract or fold such as arteries, or respiratory tract. Conduits such as in the gastro-intestinal or genito-urinary tract tend to fold when they are not filled, even when gas or fluid under pressure is introduced, and this issue may create problems with the retractile-swivel method, since in an organ with folded walls there will be areas that will remain non-investigated. Hence a method that will put pressure on and so unfold the organ's walls followed by simultaneous and multiple point-contact measurements will have the greatest success of covering the organ of interest in any type of cavitary organs.

Using a punch-ball membrane, one can attach a multiplicity of sensors on the exterior surface of the membrane. When deployed inside a cavitary organ under the action of an extension force, the punch-ball will exert a pressure on the cavity's wall and completely unfold the organ's walls creating premises for optimal data acquisition. The punchball in this type of embodiment will have spectroscopic, optical or ultrasound sensors mounted on the external surface of the membrane, and optimally acquire data from the entire surface of the cavitary organ of interest, while at the same time not obstructing the transit of fluids or solids through the particular cavity. After the data has been acquired the extension force will be discontinued, the punch-ball membrane will come to a resting non-deployed state and then will be removed from the body.

To exemplify version 2, one can imagine the use of punch-ball in any type of non-biological structures to seal or support structures that are damaged or being raised.

EXAMPLE 5

Figure 6:
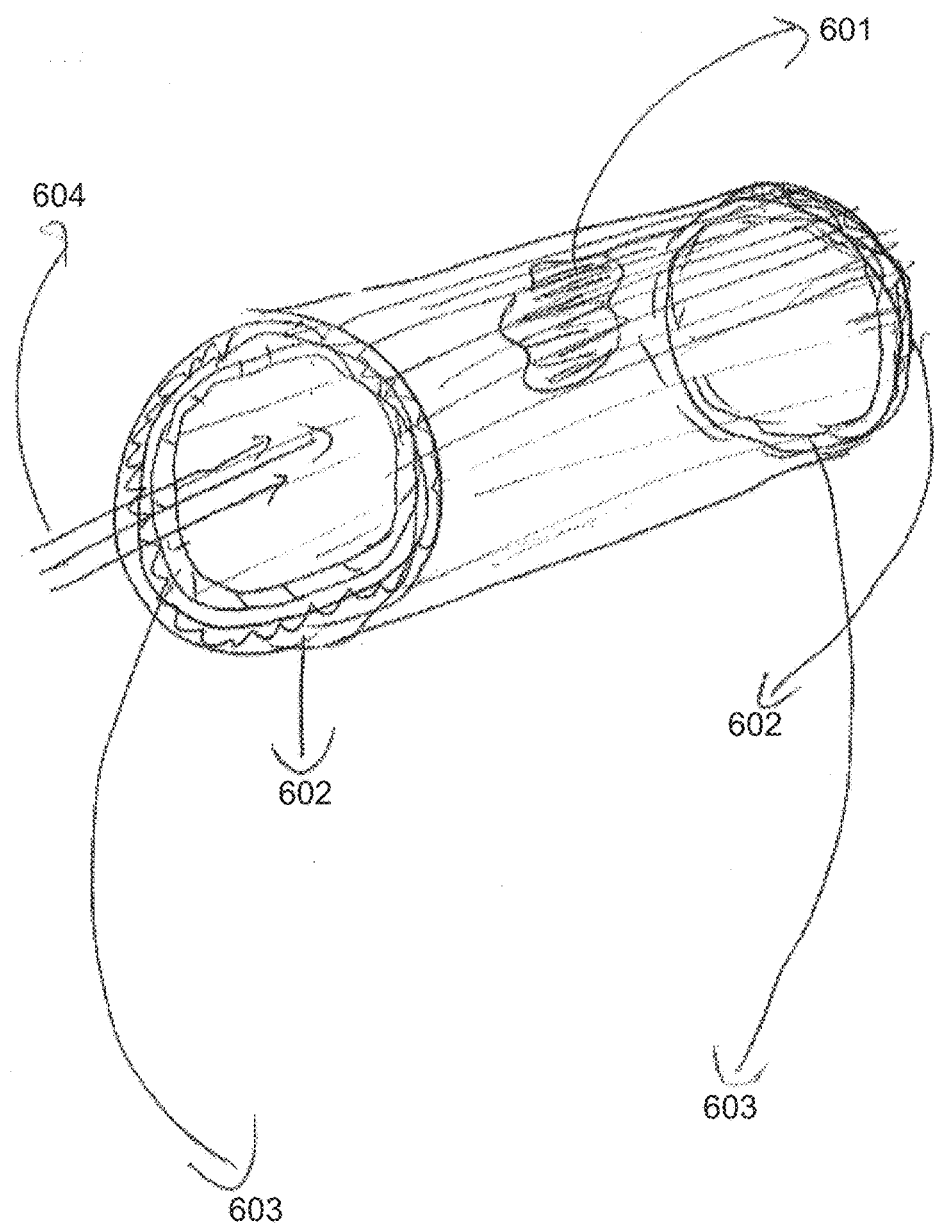
FIG. 6. Use of a punch-ball in the process of fixing a puncture damage in a pipeline, while fluids are still being transferred through the latter.

Damaged pipelines would be the first example. In the case of punctured pipelines where immediate relief is needed, mostly when the location of the puncture is not known, one can imagine the use of a punch-ball to seal the possible puncture. If the operator suspects which is the segment of the pipeline where the puncture is located, then he or she can thread a punch-ball wire with a punch ball longitudinally attached to it from one end of the segment to the other followed by application of an extension force in the punch-ball and expansion of the punch-ball. The punch-ball will cover completely the lateral walls of the pipeline with sealing of the puncture, to stop the loss and fluid from the pipeline, while the pipeline is being fixed. In this case the punch-ball will be a tubular structure with a continuous side-wall in order to perform an appropriate seal, with punches accommodated only at the beginning and end of the structure in order to allow transit of fluids to continue through the pipeline while the puncture is sealed. (FIG. 6). FIG. 6 includes: puncture damage 601; pipe walls 602; punch-ball covering the inside of the damaged pipe and the puncture damage 603; and Flow continuing through the punch-ball's empty space 604.

One can imagine that a patch can be deployed to seal the puncture, patch that is initially partially adherent to the punch-ball, that subsequently adheres to the pipe, and that in a terminal stage is peeled off from the punch-ball and staying on the inside wall of the pipe, all this while the flow inside the pipeline continues unobstructed. After the damage has been fixed the extension force will be discontinued in the version where the deployment is just temporary, the punch-ball membrane will come to a resting non-deployed state and then it will be removed from the pipeline.

EXAMPLE 6

Figure 7:
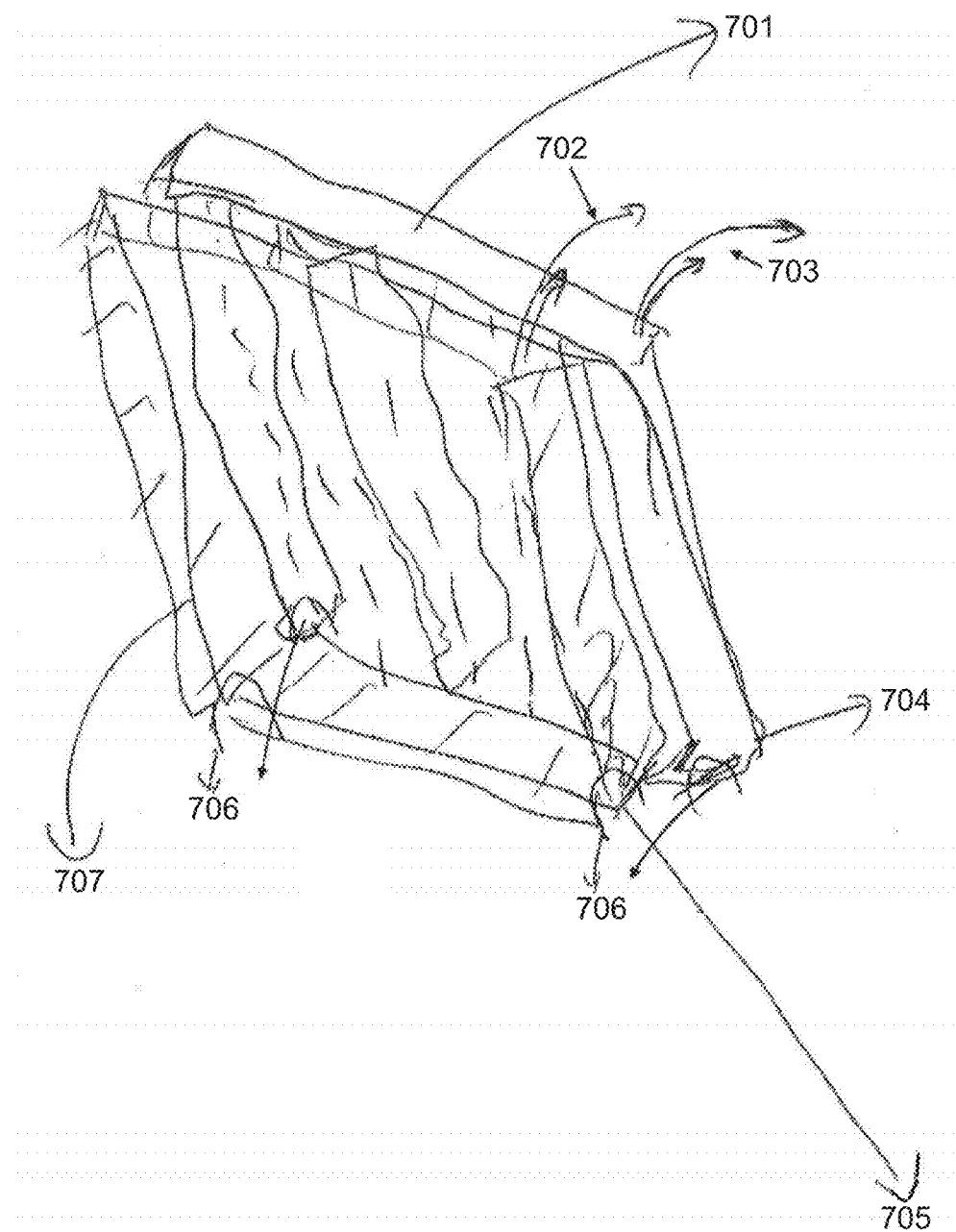
FIG. 7. Punch-ball used for elevating a construction structure.

Another way to use a punch-ball is as temporary support in construction, such as but not limited to lending support for and lifting concrete and steel castings, where exact positioning, durability and repeatability, as well as fast mounting and dismounting are very important (FIG. 7). FIG. 7 includes: construction parts such as made of concrete or steel/iron 701; lifting motion of the punch-ball 702; simultaneous motion of the construction part 703; construction part anchored in the floor 704; punch-ball anchored in the floor 705; anchors 706; and punch-ball membrane used to lift and keep construction part in place 707.

The advantages of this method among others are the ability to raise several casting parts at the same time in order to ensemble them together, and the obvious possibility of being able to avoid the use of heavy equipment such as cranes.

The use in this version is temporary, when the punch-ball only supports the casting, or can be permanent. In the former option, after the intended part of the construction (such as raising a concrete casting) has finished, the extension force will be discontinued, the punch-ball membrane will come to a resting non-deployed state and then it will be removed. In the latter option, the punch-ball's central empty space will be filled with the material that will give structure to the segment of the construction, such as concrete. The construction material will be introduced inside the empty space of the punch-ball (FIG. 8) in this later version and will surround the metal part of the casting. In this way concrete will pour in the empty space and incorporate the metal part.

The latter version of the use on punch-ball construction may be specifically interesting in underwater construction, where a fast deployment of casting might be necessary and can be achieved by the punch-ball's rather instant deployment mechanism, after the membrane has been initially attached securely to the bottom of the river, sea or lake.

In general in most of the applications of category A, the use of the punch-ball has a limited temporary use. After the punch-ball action is not needed anymore, the punch-ball membrane will come to a resting non-deployed state and then it will be removed from the cavity where it was inserted into or removed from the place of the action.

Category B. The punch-ball can be used in an instance where it will not support an outside structure and will function all by itself. One can imagine constructing long tubes for transit of materials or people that can deploy fast and can be stored in small spaces. These transit tubes have to be made a very thin and durable material, in order to be able to store in a small space and at the same time to be able to endure high stress forces. The tubes will have at least two punches, at the beginning and the end of the structure, to allow transit and function by a self-expanding principle enunciated at the beginning of the patent application. Possible uses of such structures could be the evacuation of people from tall buildings in danger of immediate collapse, or from damaged under-water vehicles, when immediate deployment is necessary and a small space of storage prior to deployment is needed. More common applications such as transferring objects in a building between various rooms can be envisioned as well. By instantly deploying or closing trough the mechanisms listed at the beginning of this invention various elements of such a system, one can control the direction through which the objects will transfer. With our method several transfer tubes can be stored in the same space while in the 'shrunken' state, and deployed only when needed, which can offer the option of several transit directions using the same storage space.

Figure 8:
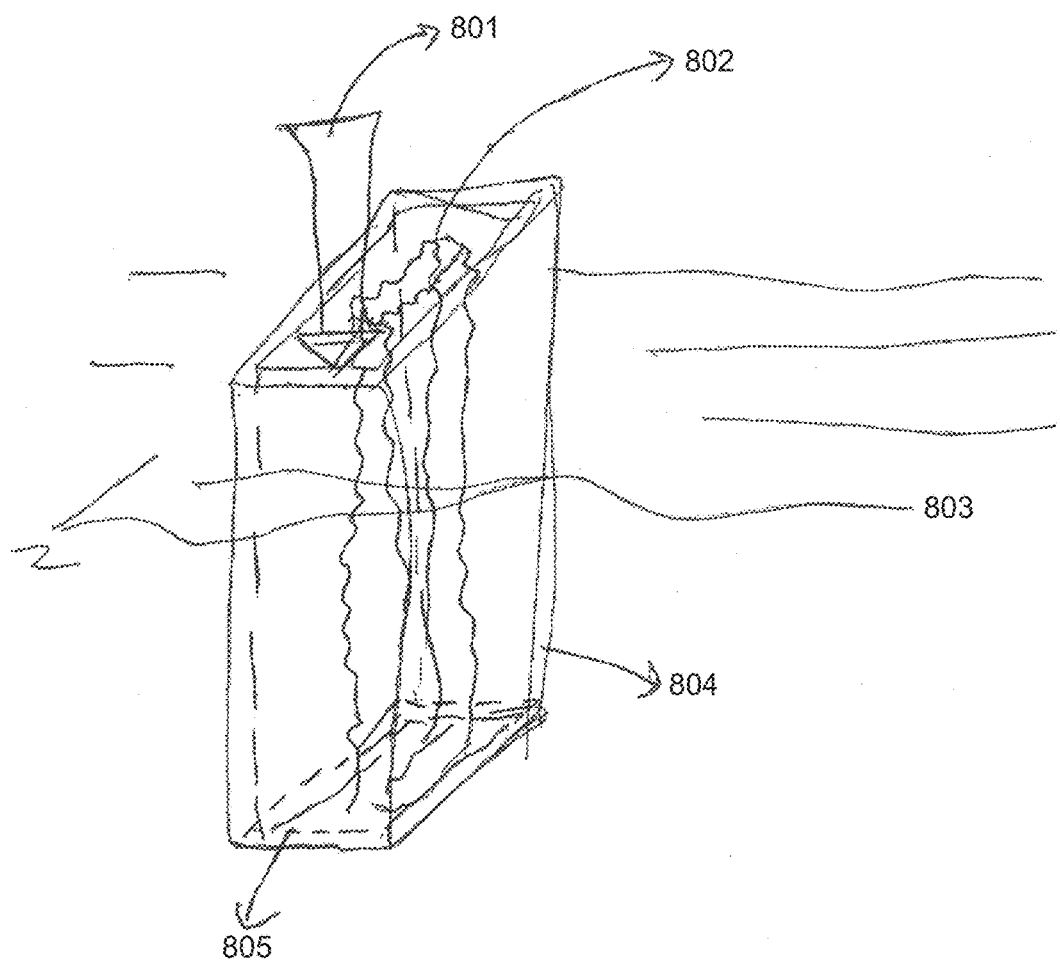
FIG. 8. Punch-ball anchored on a river bed and used to erect a bridge structure inside the flowing waters of a river or lake.
Figure 9:
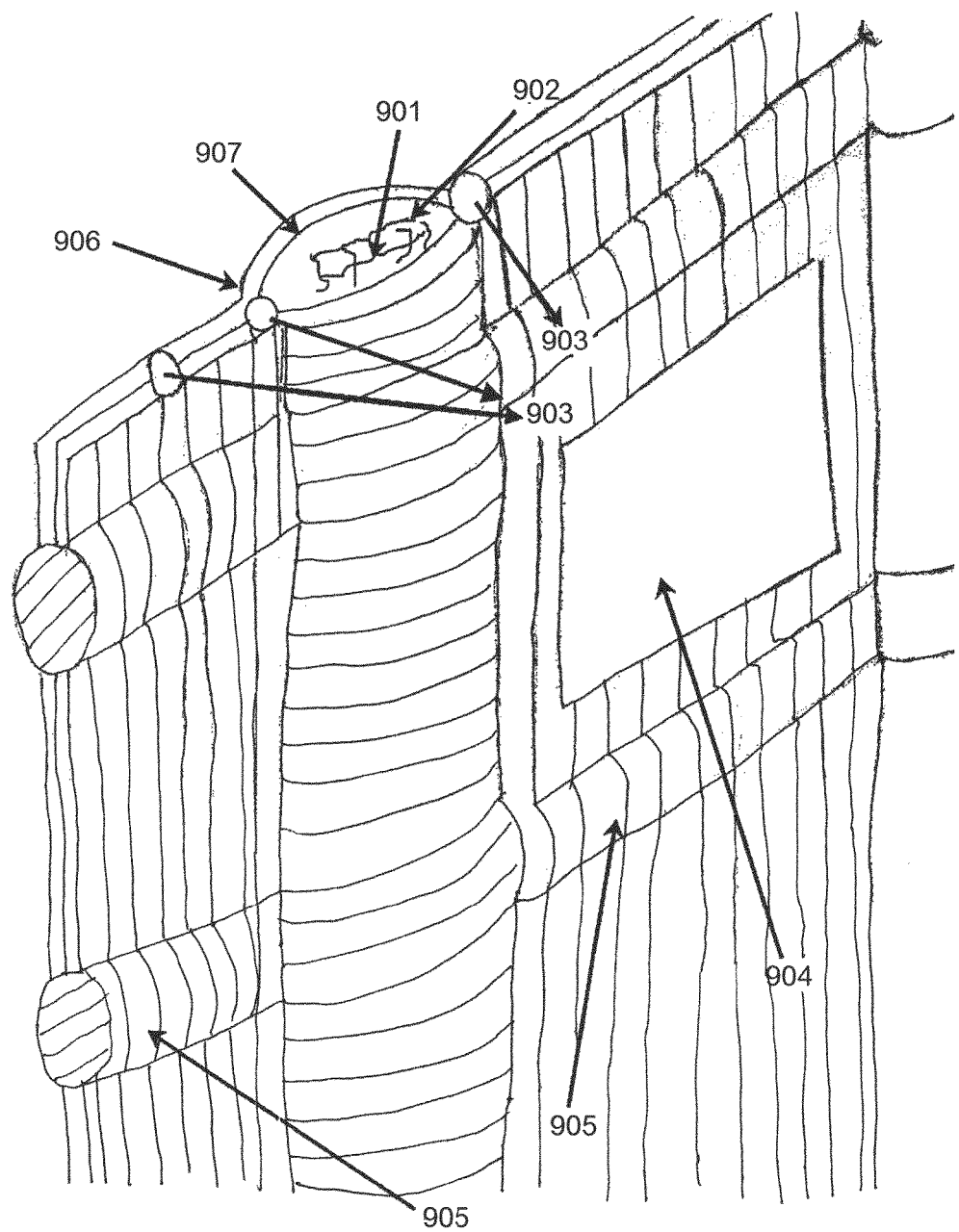
FIG. 9. A punch-ball system used on a construction site. The punch-ball is initially extended by using any of the four mechanisms presented in the application. In this example the extension is produced by introducing under pressure a fluid through numerous channels. Then construction material such as concrete can be poured in the punch-ball's empty spaces through the punch-ball inlets.

Another application would be in the toys or construction industry, where one can build self-expandable structure of temporary or even permanent use and with shapes that would not be possible otherwise. For example a ball where there is no camera inside. The camera is represented by the punch-ball which is a thin chamber (less than 5 mm for example for a ball with a diameter greater than 20 cm) that covers the entire spherical surface of the ball. Because there is no internal camera, one can image offering various patterns to this type of ball where empty space scan be created in its surface. Other possibilities of use will include complicated architecture toys, including doll houses, toy palaces, etc., that can be built in great detail, due to the thin nature of the punch-ball membrane and it ability to take various shapes. Also real-size architectural buildings can be imagined, with the advantage of being stored in a small volume prior to expanding, fast expanding and deactivation and then storage times. While inflatable living spaces are already used commercially (for example, http://www.treehugger.com/sustainable-product-design/inflatable-teahouse-by-kengo-kuma.html), the obvious disadvantage of these structures is that the puncturing damage (that is a random, possibly frequent event) to the inflatable membrane can prevent the inflation. Other mechanism to extend the membrane, and listed in this invention such as using a membrane including electro-active polymers or electromagnets can prevent the above fallout. Yet another application of this category would be in construction where the punchball's central empty space will be filled with the material that will give structure to the segment of the construction, such as concrete, while the punch-ball protects the construction material from the outside environment such as the water of river or lake. The construction material will be introduced inside the empty space of the punch-ball (FIG. 8) in this later version and will surround the eventual metal/concrete part of the construction that lends resistance to the entire structure. In this way concrete will pour in the empty space and incorporate/surround the eventual metal part. FIG. 8 includes: concrete or cement being poured inside the punchball empty space through the punch-ball inlet 801; iron/steel part built inside the punch-ball empty space 802; pool of water (such as lake or river) 803; punch-ball apparatus anchored on water-bed and elevated from the ground up 804; and Site of punch-ball being anchored on the water-bed 805. In another application of an independent use of a punch-ball the latter can be used as a way to lend shape to other concrete structures such as concrete tubular networks that form the structure of a wall as presented in FIG. 9. FIG. 9 includes: inlet of empty space of punch-ball that allows construction materials such as concrete to be poured into the empty space 901; metal construction part 902; channels that allow an extension fluid to extend the punch-ball prior to the construction material being poured in 903; punches such as a small window in this example 904; ramifications of the punch-ball's empty space allowing construction material to spread throughout the punch-ball's surface 905; external surface of punch-ball 906; and internal surface of punch-ball 907.

The empty space in this case can be raised around the metal structures that give resistance to the wall and when the membrane is under tension through the four mechanisms presented in this application one can pour construction materials (concrete) in the punch-ball's empty space. The punch ball can be supported connecting it—after extending it—with the metal construction structure. Subsequently when the concrete solidifies the latter will take the shape imprinted by the punch-ball.

The following are some objects the invention:

The present invention's goal is to devise an apparatus (here-forth called 'punch-ball') made of a thin tension-reversible membrane that:
  a) will actively expand and assume a particular three-dimensional predetermined shape when under a tension force
  b) will passively or actively shrink to the initial resting shape when the tension force ceases
  c) will border a central empty space
  d) have an interior face bordering the central empty space
  e) have an exterior face bordering the exterior space of the membrane
  f) display direct communications between central space and the exterior space of the membrane, outside of the external face of the 'punch-ball', through orifices in the membrane (here-forth called 'punches'), punches that will not decrease the ability of the membrane to exhibit a tension force.
  g) at the end of the action performed will be in general un-deployed by stopping the extension force in the punch-ball, followed by removal of the punch-ball from the location of action.

The system defined above can be used freestanding or in connection with an object representing a confined space that will be abutting the exterior face of the punch-ball when the punch-ball is under tension.

The system (punch-ball) defined above with openings in the membrane that will allow fluid to flow freely or solids to be transferred freely between the interior and exterior of the system without any limitations to the initial flow through the cavity prior to the punch-ball membrane being deployed in the cavity, the interior face of the membrane being defined as surrounding the empty space inside the punch-ball while the exterior face of the membrane as facing the exterior of the punch-ball.

The punch-ball defined above will be provided with hinge borders (hinge borders that will lack partially or completely the property of being under tension, and at same time have various degrees of elasticity or deformability), borders that will allow the punch-ball shape to adapt to the shape of the cavity in which it will be deployed, or for the action to be undertaken.

The walls of the punch-ball system defined above will be made of a membrane supposed to be a thin membrane (thickness less than approximately ⅕ of the average diameter of the empty space that the membrane surrounds)

The material membrane that the punch-ball from above is made of has to have high tensile strength (this will allow pressure with little deformation of the material, allowing the empty space that the punch ball surrounds not to occlude), medium elasticity, and allow processing into thin sheets finally rendering a thin membrane. Polyethyleneterphtalate and carbon nanotubes may be two such materials.

The punch-ball system from above when deployed will uniformly circumferentially touch the walls of the cavity in which they will be introduced at least in one plane of the three-dimensional space.

When deployed in a cavity, the punch-ball system from above will allow the transfer the fluids or solids through its empty space, by being provided with punches approximately similar with the inlets and the outlets of the cavity in which they will be deployed.

A first method to activate a tension force in a punch-ball system such as described above would be to embed in a thin layer made of plastic material or any other material that can be subjected to processing into thin sheets, electro-magnetic coils of various thicknesses (such as centimeters, millimeters, microns or nanometers), sizes that correlate with the thickness of the plastic layer; the application of a current into the coils in such a way to create magnetic fields of similar or opposite directions will result into a reciprocal force of repulsion or attraction of the electromagnets, resulting into an immediate tension and stretching or shrinking of the membrane and subsequent expansion or shrinking respectively.

Another method to activate a tension force in a punch-ball system such as described above would be to employ thin sheets of shape-changing metals or plastics that could be incorporated into the membranes that are supposed to expand, or by incorporating into the particular membranes a multitude of threads that self-expand spontaneously and then retract upon manual or automatic retraction.

Still another method to activate a tension force in a punch-ball system such as described above is to incorporate inside a thin sheet or multiple sheets of plastic or polymeric materials, electro-active polymers that, by changing shape or dimensions in various directions upon application of a voltage, can change the shape and tension of the membrane.

A fourth method to activate a tension force in a punch-ball system such as described above is to use polymeric plastic material sheet with multitude of vacuolated spaces inside the thickness of the membrane, all in communication with each other, empty spaces that have the purpose of being filled with a fluid under pressure and in this way exerting a tension force in the plane of the membrane.

In one embodiment the punch-ball system will be used in connection with a confined cavitary space by covering partially or completely the internal surface of the particular objects encircling the confined cavitary space with the purpose of putting pressure on the objects that encircle that particular cavitary space or to obliterate orifices inadvertently created in the objects that encircle the particular confined cavitary space, without limiting or obstructing the space confined, and at the same time allowing fluids to freely flow from outside to the inside (and also in the opposite direction) of the confined cavitary space or solid objects to freely transfer from outside to the inside (and also in the opposite direction) of the confined cavitary space.

The system will place high pressures on the walls of the confined cavitary space such as in industrial applications, or pressures of low magnitude as well, such as in medical applications.

A method to activate a tension force in the membrane of the punch-ball application by introducing a fluid under pressure between the layers of a punch-ball membrane made of two separate layers with the two layers attaching to each other in defined areas by fusion, gluing or melting or any other process or come in contact by fibers that interwove between the two layers, with a distance between the layers approximately less than 1/10 of the average diameter of the empty space that the membrane surrounds.

In one embodiment one would like to use of punch-ball system inside anatomical cavitary organs, and in a second embodiment in any mechanical domain where one would like to create a support for an outside structure or create a seal for an outside structure that inadvertently suffered unwanted punctures or damages.

The first application of the anatomical embodiment is the occasion of an electrophysiological arrhythmia ablation, where by using a punch-ball system one would cover the heart chamber uniformly, and due to the fact that the membrane allows open areas (punches) to be left in its surface, still allow the blood to flow through that particular cardiac cavity while the procedure takes place, giving enough time to the operator to deploy the punch-ball, send the diagnostic stimuli, reach a diagnosis and then perform an ablation by deploying the burning stimuli (which in general are radiofrequency or cryoablation stimuli).

The second application of the anatomical embodiment is use of a punch-ball system in human or animal vessels (arteries, veins), that can be exemplified by use of this device in the case of aortic dissection, or any tubular organs of the body.

One can imagine the use of a punch-ball as being in the shape of a long tubular punch-ball system with the external diameter similar in size with the lumen of the aorta that can be in the resting position disposed around a wire, which can be introduced in the aorta through a sheath and a catheter by ways of a peripheral artery, and then when decided that punch-ball is in appropriate position, the punch-ball is to be deployed, putting pressure on the aortic walls, and pressing the blood out of the false lumen; due to numerous punches in the lateral walls the punch-ball allows continuous irrigation of the organs that the aorta distributes blood to, prior to arrival to a tertiary care center where aortic surgery will be preformed.

The system and method of using a punch-ball system adjusted to deploying a patch onto a bodily cavitary wall, with the purpose of covering uniformly and completely a congenital or acquired puncture orifice in this particular wall.

Alternatively one can imagine a way to keep the punch-ball for a certain prolonged period of time in the aorta and allow the intima to re-adhere to the media without surgery.

Other applications similar with the application include but not limited to aortic transsection, and arterial or venous dissections other than aortic dissection.

Since the punch-ball can make complete contact with a tubular structure without occluding the particular structure, one can imagine the possibility of delivering drugs to that particular cavitary anatomical structure by using the punch-ball system, by maintaining the punch-ball system expanded in the particular cavity for a relatively longer period of time, and delivering the drug through the intermediation of microscopic needles or through pressure transfer from pores in the external surface of the punch-ball into the walls of the cavity.

One also can imagine the use the punch-ball system as in the method described by simply placing pressure for a long time on the walls of cavitary organs, with the purpose for example of stopping a bleeding from a bleeding vessel inside the organ's walls, while fluids and solids still can transfer though the cavity.

Another reason to use a punch-ball inside any of the cavitary organs as described is to make simultaneous multiple measurements that require close contact, such as spectroscopy, optical and ultrasound measurements.

Another way to use a punch-ball as in the method described is to use it as temporary support in construction, such as but not limited to lending support for concrete castings or being the actual casting, where exact positioning, durability and repeatability, as well as fast mounting and dismounting are very important.

One can imagine the use of punch-ball in any type of non-biological structures as described to seal or support industrial structures that are damaged by puncture, with initial insertion of the punch-ball inside the damaged cavitary structure, followed by application of an extension force in the punch-ball and expansion of the punch-ball, which will cover completely the lateral walls of the cavity with sealing of the puncture while the cavity is being fixed and eventually allow application of a patch on the inside wall of the pipeline for temporary of permanent fix of the puncture, and at the same time and allow transit of fluids to continue through the cavity while the puncture is sealed.

In a second embodiment of the punch-ball system, the system can be used in an instance where it will not support an outside structure and will function all by itself.

One can use the punch-ball system by constructing long tubes for transit of materials or people that can deploy fast and can be stored in small spaces, transit tubes have made of a very thin and durable material, in order to be able to store in a small space and at the same time to be able to endure high stress forces.

Possible uses of such transit structures could be the evacuation of people from tall buildings in danger of immediate collapse, or from damaged under-water vehicles, when immediate deployment is necessary and a small space of storage prior to deployment is needed.

Another application of system is the transfer of objects or people in a building between various rooms, by instantly deploying or closing various elements of a tubular transfer system, controlling in this way the direction through which the objects or people transfer, with multiple transfer tubes being stored in the same space while in the shrunken state, thus offering the option of several transit directions using the same storage space.

Another application of the embodiment would be in the toys or construction industry, where one can build self-expandable structure of temporary or permanent use.

For example, a toy built is a ball where there is no inflatable balloon structure inside, with the expandable structure being represented by the punch-ball which is a thin membrane (less than 1 cm for example for a ball with a diameter greater than 20 cm) that covers the entire spherical surface of the ball, with various design patterns where empty space scan be created in its surface without affecting the expandable quality of the ball.

Other possibilities of use of punch-ball devise described include complicated architecture toys, including doll houses, toy palaces, etc., that can be build in great detail, due to the thin nature of the punch-ball membrane and it ability to take various shapes.

Also real-size architectural buildings can be imagined being built, with the advantage of being stored in a small volume prior to expanding, fast expanding and deactivation and storage times using safe and durable expanding and shrinking systems such as electro-active polymers or electromagnets.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An apparatus for supporting and uniformly covering at least in one plane a cavity structure without obstructing the flow of fluid through the cavity structure, the apparatus comprising:
   an expandable membrane configured to transition between an expanded state and a shrunken state, wherein the membrane is comprised of a first layer and a second layer, the edges of which are joined together to create a closed chamber between the first layer and the second layer, the membrane comprising:
   an internal face and an external face opposite the internal face;
   a tension mechanism disposed between the internal face and the external face and configured to exert force on the first layer and the second layer to place the expandable membrane in the expanded state;
   and at least one orifice disposed between the internal face and the external face, wherein the external face is in fluid communication through the orifice with an empty space defined by the internal face of the membrane when the membrane is in the expanded state.

2. The apparatus of claim 1, further comprising one or more tubes connected to the closed chamber, wherein the tension mechanism comprises the one or more tubes and a pressurized fluid received in the closed chamber through the one or more tubes.

3. The apparatus of claim 1, wherein the tension mechanism comprises a plurality of electromagnets.

4. The apparatus of claim 1, wherein the tension mechanism comprises one or more sheets or threads of spontaneously shape-changing metal or plastic.

5. The apparatus of claim 1, wherein the tension mechanism comprises one or more sheets of electro-active polymers that expand upon the application of a voltage.

6. The apparatus of claim 1, wherein the rate of flow of fluid through the cavity structure when the membrane is in the expanded state is approximately equal to the rate of flow of fluid through the cavity structure when the membrane is in the shrunken state.

7. The apparatus of claim 1, wherein the first layer and second layer are attached to each other by fusion, gluing, melting, by fibers interwoven between the first layer and second layer, or by allowing the first and second layer to continue with each other.

8. The apparatus of claim 1, wherein the expandable membrane has a thickness less than approximately $\frac{1}{5}$ of an average diameter of the empty space.

9. The apparatus of claim 1, wherein removal of the force exerted by the tension mechanism places the membrane in the shrunken state.

10. The apparatus of claim 1, further comprising at least one hinge, wherein the at least one hinge is configured to not be under tension when the membrane is in the expanded state.

* * * * *